US010189952B2

(12) United States Patent
Bowman et al.

(10) Patent No.: US 10,189,952 B2
(45) Date of Patent: *Jan. 29, 2019

(54) DEGRADABLE THIOL-ENE POLYMERS

(71) Applicant: Regents of the University of Colorado, A Body Corporate, Denver, CO (US)

(72) Inventors: Christopher Bowman, Boulder, CO (US); Kristi Anseth, Boulder, CO (US); Bilge Hacioglu, Boulder, CO (US); Charlie Nuttelman, Boulder, CO (US)

(73) Assignee: REGENTS OF THE UNIVERSITY OF COLORADO, A BODY CORP, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,939

(22) Filed: Mar. 16, 2017

(65) Prior Publication Data

US 2017/0247541 A1   Aug. 31, 2017

Related U.S. Application Data

(60) Continuation of application No. 14/848,141, filed on Sep. 8, 2015, now Pat. No. 9,631,092, which is a continuation of application No. 14/485,490, filed on Sep. 12, 2014, now abandoned, which is a continuation of application No. 13/951,268, filed on Jul. 25, 2013, now Pat. No. 8,859,716, which is a continuation of application No. 12/556,640, filed on Sep. 10, 2009, now Pat. No. 8,519,086, which is a division of application No. 11/858,062, filed on Sep. 19, 2007, now abandoned, which is a division of application No. 10/269,916, filed on Oct. 10, 2002, now Pat. No. 7,288,608.

(60) Provisional application No. 60/328,669, filed on Oct. 10, 2001.

(51) Int. Cl.

| | |
|---|---|
| C08G 75/04 | (2016.01) |
| C08G 75/045 | (2016.01) |
| C08L 89/00 | (2006.01) |
| C08G 81/02 | (2006.01) |
| C08G 81/00 | (2006.01) |
| C08L 71/02 | (2006.01) |
| C08L 81/02 | (2006.01) |
| A61L 27/16 | (2006.01) |
| A61L 27/18 | (2006.01) |
| A61L 27/52 | (2006.01) |
| A01N 25/04 | (2006.01) |
| A61L 27/38 | (2006.01) |
| A61L 27/54 | (2006.01) |
| C05G 3/00 | (2006.01) |
| A61K 47/34 | (2017.01) |
| C08J 3/075 | (2006.01) |

(52) U.S. Cl.
CPC .......... *C08G 75/045* (2013.01); *A01N 25/04* (2013.01); *A61K 47/34* (2013.01); *A61L 27/16* (2013.01); *A61L 27/18* (2013.01); *A61L 27/38* (2013.01); *A61L 27/52* (2013.01); *A61L 27/54* (2013.01); *C05G 3/0029* (2013.01); *C05G 3/0076* (2013.01); *C08G 81/00* (2013.01); *C08G 81/025* (2013.01); *C08G 81/027* (2013.01); *C08J 3/075* (2013.01); *C08L 71/02* (2013.01); *C08L 81/02* (2013.01); *C08L 89/00* (2013.01); *A61L 2300/62* (2013.01); *C08G 2261/126* (2013.01); *C08J 2329/04* (2013.01); *C08J 2367/04* (2013.01); *C08J 2371/02* (2013.01); *C08L 2205/05* (2013.01); *Y10S 524/916* (2013.01); *Y10S 525/936* (2013.01)

(58) Field of Classification Search
None
See application file for complete search history.

(56) References Cited

U.S. PATENT DOCUMENTS

| | | | |
|---|---|---|---|
| 3,920,877 A | 11/1975 | Barber et al. |
| 4,081,598 A | 3/1978 | Morgan et al. |
| 4,808,638 A | 2/1989 | Steinkraus et al. |
| 4,969,998 A | 11/1990 | Henn |
| 5,177,056 A | 1/1993 | Hilti et al. |
| 5,399,624 A | 3/1995 | Glaser et al. |
| 5,410,016 A | 4/1995 | Hubbell et al. |
| 5,496,872 A | 3/1996 | Constancis et al. |
| 5,730,601 A | 3/1998 | Bowman et al. |
| 5,837,751 A | 11/1998 | Jacobine et al. |
| 5,858,746 A | 1/1999 | Hubbell et al. |
| 6,060,582 A | 5/2000 | Hubbell et al. |

(Continued)

FOREIGN PATENT DOCUMENTS

| | | |
|---|---|---|
| GB | 588018 A | 5/1947 |
| JP | 363280711 A | 11/1988 |

(Continued)

OTHER PUBLICATIONS

Anderson, S.B. et al. (May 2011). "The Performance of Human Mesenchymal Stem Cells Encapsulated in Cell-Degradable Polymer-peptide Hydrogels," *Biomaterials* 32:3564-3574.

(Continued)

*Primary Examiner* — Marc S Zimmer
(74) *Attorney, Agent, or Firm* — Morrison & Foerster LLP

(57) ABSTRACT

A thiol-ene polymeric material is disclosed. The material is produced by the photopolymerization of reactants having thiol and olefin moieties. The material can incorporate encapsulated components, including cells. Additionally, the material can be derivatized by reacting the polymeric material with components such as proteins.

45 Claims, 3 Drawing Sheets

(56) References Cited

U.S. PATENT DOCUMENTS

| | | | |
|---|---|---|---|
| 6,169,126 B1 | 1/2001 | Szum et al. |
| 7,018,655 B2 | 3/2006 | Lele et al. |
| 7,288,608 B2 | 10/2007 | Bowman et al. |
| 7,744,912 B1 | 6/2010 | Hubbell et al. |
| 7,842,667 B2 | 11/2010 | Seliktar et al. |
| 8,519,086 B2 | 8/2013 | Bowman et al. |
| 8,859,716 B2 | 10/2014 | Bowman et al. |
| 9,631,092 B2 | 4/2017 | Bowman et al. |
| 9,987,393 B2 | 6/2018 | Anseth et al. |
| 9,988,433 B2 | 6/2018 | Kazantsev et al. |
| 10,016,505 B2 | 7/2018 | Mariner et al. |
| 2002/0004537 A1 | 1/2002 | Krongauz et al. |
| 2002/0076443 A1 | 6/2002 | Stein et al. |
| 2004/0086479 A1 | 5/2004 | Grinstaff et al. |
| 2004/0091462 A1 | 5/2004 | Lin et al. |
| 2005/0244393 A1 | 11/2005 | Philippart et al. |
| 2006/0029578 A1 | 2/2006 | Hoemann et al. |
| 2006/0204582 A1 | 9/2006 | Stein et al. |
| 2007/0248567 A1 | 10/2007 | Pathak et al. |
| 2009/0311338 A1 | 12/2009 | Pathak et al. |
| 2009/0324720 A1 | 12/2009 | He et al. |
| 2010/0137510 A1 | 6/2010 | Seliktar et al. |
| 2010/0178355 A1 | 7/2010 | Hoemann et al. |
| 2010/0233246 A1 | 9/2010 | Sehl et al. |
| 2010/0291357 A1 | 11/2010 | Polizzotti et al. |
| 2010/0304338 A1 | 12/2010 | Cramer et al. |
| 2012/0225101 A1 | 6/2012 | Kao et al. |
| 2012/0202263 A1 | 8/2012 | Blakely et al. |
| 2013/0197189 A1 | 8/2013 | Aimetti et al. |
| 2013/0243878 A1 | 9/2013 | Mariner et al. |
| 2014/0038826 A1 | 2/2014 | Anseth et al. |
| 2014/0039085 A1 | 2/2014 | Bowman et al. |
| 2014/0112960 A1 | 4/2014 | Lin |
| 2014/0273153 A1 | 9/2014 | Kazantsev et al. |
| 2015/0133302 A1 | 5/2015 | Bowman et al. |
| 2016/0068639 A1 | 3/2016 | Bowman et al. |
| 2018/0043030 A1 | 2/2018 | Kazantsev et al. |

FOREIGN PATENT DOCUMENTS

| | | |
|---|---|---|
| WO | WO-2009/039307 A2 | 3/2009 |
| WO | WO-2012/103445 A2 | 8/2012 |
| WO | WO-2012/103446 A3 | 8/2012 |
| WO | WO-2013/116791 A1 | 8/2013 |
| WO | WO-2016/130573 A2 | 8/2016 |

OTHER PUBLICATIONS

Athanasiou, K.A. et al. (1996). "Sterilization, Toxicity, Biocompatibility and Clinical Applications of Polylactic Acid/Polyglycolic Acid Copolymers," *Biomaterials* 17(2):93-102.

Cadée, J.A. et al. (Jun. 5, 2000). "In Vivo Biocompatibility of Dextran-Based Hydrogels," *J Biomed Mater Res.* 50(3):397-404.

Chalker, J.M. et al. (2009). "Enabling Olefin Metathesis on Proteins: Chemical Methods for Installation of S-Allyl Cysteine," *Chem. Commun., The Royal Society of Chemistry* pp. 3714-3716.

Conte, M.L. et al. (2001). "Multi-Molecule Reaction of Serum Albumin Can Occur Through Thiol-Yne Coupling," *Chemical Communications* 47:11086-11088.

Cramer, N.B. et al. (2003). "Thiol-Ene Photopolymerization Mechanism and Rate Limiting Step Changes for Various Vinyl Functional Group Chemistries," *Macromolecules* 36:7964-7969.

Dondoni, A. et al. (2009)., "A New Ligation Strategy for Peptide and Protein Glycosylation: Photoinduced Thiol-Ene Coupling," *Chemistry—A European Journal* 15:11444-11449.

Draye, J.-P. et al. (Sep. 1998). "In Vitro and in Vivo Biocompatibility of Dextran Dialdehyde Cross-linked Gelatin Hydrogel Films," *Biomaterials* 19(18):1677-1687.

European Office Action for Application 13743245.6 dated Jan. 18, 2017, 5 pages.

Fairbanks, B.D. et al. (2009). "Thiol-Yne Photopolymerizations; Novel Mechanism, Kinetics, and Step-Growth Formation of Highly Cross-Linked Networks," *Macromolecules* 42:211-217.

Fairbanks, B.D. et al., (2010) "Reaction Rates and Mechanisms for Radical, Photoinitated Addition of Thiols to Alkynes, and Implications for Thiol-Yne Photopolymerizations and Click Reactions," *Macromolecules* 43:4113-4119.

Final Office Action dated Jun. 5, 2006, for U.S. Appl. No. 10/269,916, filed Oct. 10, 2002, 7 pages.

Final Office Action dated Mar. 10, 2009, for U.S. Appl. No. 11/858,062, filed Sep. 19, 2007, 6 pages.

Final Office Action dated May 31, 2011, for U.S. Appl. No. 12/556,640, filed Sep. 10, 2009, 5 pages.

Final Office Action dated Sep. 14, 2012, for U.S. Appl. No. 12/556,640, filed Sep. 10, 2009, 10 pages.

Final Office Action dated Nov. 30, 2015, for U.S. Appl. No. 13/981,885, filed Oct. 9, 2013, 17 pages.

Final Office Action dated Jan. 29, 2016, for U.S. Appl. No. 14/210,106, filed Mar. 13, 2014, 11 pages.

Final Office Action dated Oct. 3, 2016, for U.S. Appl. No. 13/758,942, filed Feb. 4, 2013, 11 pages.

Floyd, N. et al., (2009). "Thiyl Glycosylation of Olefinic Proteins: S-Linked Glycoconjugate Synthesis", *Angewandte Chemie International Edition* 48:798-7802.

Fu, Y. et al., (Aug 2011) "In situ forming poly ( ethylene glycol)-based hydrogels via thiol-maleimide Michael-type addition," *J. Biomed. Mater. Res.* 98(2):201-211.

Fu, Y. et al. (Jan. 2012), "3D Cell Entrapment in Crosslinked Thiolated Gelatin-poly(ethylene glycol) Diacrylate Hydrogels," *Biomaterials* 33(1):48-58.

Gallez, B. et al. (Jul. 1998). "Small Particles of Fusinite and Carbohydrate Chars Coated with Aqueous Soluble Polymers: Preparation and Applications for In Vivo EPR Oximetry," *Magn Reson Med.* 40(1):152-159.

Geyer, U. et al. (1994). "Formation, Derivatization and Applications of Bacterial Cellulose," *Int. J. Biol. Macromol.* 16(6):343-347.

Hernandez, K. et al. (2011). "Control of Protein Immobilization: Coupling Immobilization and Site-directed Mutagenesis to Improve biocatalyst or Biosensor Performance" *Enzyme & Microbial Technology* 48:107-122.

Hoyle, C.E. et al. (2004). "Thiol-Enes: Chemistry of the Past with Promise for the Future" Journal of Polymer Science: Part A: *Polymer Chemistry* 42:5301-5338.

International Preliminary Report on Patentability dated Jul. 30, 2013, for PCT Patent Application No. PCT/US2012/022920, filed Jan. 27, 2012, 7 pages.

International Preliminary Report on Patentability dated Aug. 8, 2013 for PCT Patent Application No. PCT/US2012/022920, filed on Jan. 27, 2012, 8 pages.

International Search Report dated Jan. 3, 2003, for PCT Patent Application No. PCT/US02/32669, filed Oct. 10, 2002, 1 page.

International Search Report and Written Opinion dated Aug. 30, 2012, for PCT Patent Application No. PCT/US2012/022920, Internationally filed on Jan. 27, 2012, 9 pages.

International Search Report dated Apr. 11, 2013 for PCT Patent Application No. PCT/US2013/024520 filed on Feb. 1, 2013, three pages.

International Search Report dated Aug. 18, 2016, for PCT Patent Application No. PCT/US2016/17189, Internationally filed on Feb. 9, 2016, 4 pages.

Jain, R.A. (2000). "The Manufacturing Techniques of Various Drug Loaded Biodegradable Poly(lactide-co-glycolide) (PLGA) Devices," *Biomaterials* 21:2475-2490.

Jin, R. et al., (Jun. 2010). "Synthesis and characterization of hyaluronic acid-poly(enthylene glycol) hydrogels via Michael addition: An injectable biomaterial for cartilage repair," *Acta Biomaterialia* 6(6):1968-1977.

Jones, M.W. et al., (2009). "Phosphine-Mediated One-Pot Thiol-Ene "Click" Approach to Polymer-Protein Conjugates," *Chem. Commun.,* 5272-5274.

Li, Y. et al., (2012). "Genetically Encoded Alkenyl-Pyrrolysine Analogues for Thiol-Ene Reaction Mediated Site-Specific Protein Labeling" *Chemical Science* 3:2766-2770.

Lin, S.S. et al. (Aug. 30-Sep. 3, 2006). "Controlled Release of PRP-Derived Growth Factors Promotes Osteogenic Differentiation

(56) References Cited

OTHER PUBLICATIONS of Human Mesenchymal Stem Cells," *Proceedings of the 28th IEEE EMBS Annual International Conference*, New York, USA, SaA06.4:4358-4361.
Lin, C.C. et al. (2011) "PEG Hydrogels Formed by Thiol-Ene Photo-Click Chemistry and Their Effect on the Formation and Recovery of Insulin-Secreting Cell Spheroids" *Biomaterials* 32(36):9685-9695.
Lowe, A.B. et al. (2010). "Thiol-yne Click Chemistry: A Powerful and Versatile Methodology for Materials Synthesis," *Journal of Materials Chemistry*, 20:4745-4750.
Maleimide, retrieved from <www.en.wikipedia.org/wiki/Maleimides> on Mar. 3, 2012, 3 pages.
McCall, J.D. et al. (2012) "Thiol-Ene Photopolymerizations Provide a Facile Method to Encapsulate Proteins and Maintain Their Bioactivity", *Biomacromolecules* 13:2410-2417.
Moreira, H. et al. (Feb. 2000). "Use of Bioresorbable Membrane (Sodium Hyaluronate + Carboxymethylcellulose) After Controlled Bowel Injuries in a Rabbit Model," *Diseases of the Colon Rectum* 43(2):182-187.
Non Final Office Action dated Dec. 30, 2005, for U.S. Appl. No. 10/269,916, filed Oct. 10, 2002, 6 pages.
Non Final Office Action dated Aug. 6, 2008, for U.S. Appl. No. 11/858,062, filed Sep. 19, 2007, 6 pages.
Non Final Office Action dated Oct. 25, 2010, for U.S. Appl. No. 12/556,640, filed Sep. 10, 2009, 9 pages.
Non-Final Office Action dated Dec. 31, 2015, for U.S. Appl. No. 13/758,942, filed Feb. 4, 2013, 14 pages.
Non Final Office Action dated Nov. 20, 2013, for U.S. Appl. No. 13/951,268, filed Jul. 25, 2013, 9 pages.
Non-Final Office Action dated Apr. 3, 2015, for U.S. Appl. No. 13/981,885, filed Oct. 9, 2013, 16 pages.
Non-Final Office Action dated Jul. 18, 2016, for U.S. Appl. No. 13/981,885, filed Oct. 9, 2013, 18 pages.
Non-Final Office Action dated Jul. 16, 2015, for U.S. Appl. No. 14/210,106, filed Mar. 13, 2014, 10 pages.
Non-Final Office Action dated Sep. 16, 2016, for U.S. Appl. No. 14/210,106, filed Mar. 13, 2014, 12 pages.
Non-Final Office Action dated May 8, 2015, for U.S. Appl. No. 14/485,490, filed Sep. 12, 2014, 10 pages.
Non-Final Office Action dated May 19, 2016, for U.S. Appl. No. 14/848,141, filed Sep. 8, 2015, 12 pages.
Notice of Allowance dated Dec. 14, 2006, for U.S. Appl. No. 10/269,916, filed Oct. 10, 2002, 6 pages.
Notice of Allowance dated Jun. 19, 2007, for U.S. Appl. No. 10/269,916, filed Oct. 10, 2002, 6 pages.
Notice of Allowance dated Apr. 26, 2013, for U.S. Appl No. 12/556,640, filed Sep. 10, 2009, 6 pages.
Notice of Allowance dated Jun. 11, 2014, for U.S. Appl. No. 13/951,268, filed Jul. 25, 2013, 13 pages.
Notice of Allowance dated Dec. 16, 2016 for U.S. Appl. No. 14/848,141, filed Sep. 8, 2015, 7 pages.
Qiu, B. et al. (2004). "A hydrogel prepared by in situ cross-linking of a thiol-containing poly(ethylene glycol)-based copolymer: a new biomaterial for protein drug delivery," *Biomaterials* 24:11-18.

Raza, A. et al. (2013). "The Influence of Matrix Degradation and Functional on Cell Survival and Morphogenesis in PEG-Based Hydrogels," *Macromolecular Bioscience* 13:1048-1058.
Restriction Requirement dated Sep. 13, 2005, for U.S. Appl. No. 10/269,916, filed Oct. 10, 2002. 5 pages.
Restriction Requirement dated Jul. 13, 2005, for U.S. Appl. No. 10/269,916, filed Oct. 10, 2002. 9 pages.
Restriction Requirement dated Feb. 12, 2015, for U.S. Appl. No. 14/210,106 filed Mar. 13, 2014, 6 pages.
Restriction Requirement dated Aug. 31, 2015 for U.S. Appl. No. 13/758,942, filed Feb. 4, 2013, 8 pages.
Restriction Requirement dated Nov. 20, 2014 for U.S. Appl. No. 13/981,885, filed Oct. 9, 2013, 11 pages.
Roberts, J.J. et al. (2013). "Comparison of Photopolymerizable Thiol-ene PEG and Acrylate-based PEG Hydrogels for Cartilage Development," *Biomaterials* 34(38):9969-9979.
Roskos, K.V. et al. (1995). "Biocompatibility and in Vivo Morphine Diffusion into a Placebo Morphine-triggered Naltrexone Delivery Device in Rabbits," *Biomaterials* 16(16):1235-1239.
Russo, L. et al. (Mar. 2016; e-published on Dec. 9, 2015). "Gelatin Hydrogels via Thiol-ene Chemistry," *Monatshefte Für Chemie* 147(3):587-592.
Sell, S.A. et al. (Dec. 2012) "The Incorporation and Controlled Release of Platlet-Rich Plasma-Derived Biomolecules From Polymeric Tissue Engineering Scaffolds," *Polym. Int* 61(12):1703-1709.
Supplementary European Search Report dated Dec. 14, 2015, for European Patent Application No. 13743245.6, filed on Feb. 1, 2013, 10 pages.
Veronese, F.M. (2001) "Peptide and Protein PEGylation: A Review of Problems and Solutions", *Biomaterials* 22:405-417.
Wiese, K.G. (1993). "Osmotically Induced Tissue Expansion with Hydrogels: A New Dimension in Tissue Expansion? A Preliminary Report," *Journal of Cranio-Maxillo-Facial Surgery* 21:309-313.
Written Opinion dated Aug. 30, 2012, for PCT Application No. PCT/US2012/022920, filed on Jan. 27, 2012, 6 pages.
Written Opinion dated Apr. 11, 2013 for PCT Patent Application No. PCT/US/13/24520 filed on Feb. 1, 2013, 6 pages.
Written Opinion dated Aug. 18, 2016, for PCT Patent Application No. PCT/US2016/17189, Internationally filed on Feb. 9, 2016, 6 pages.
Wu, J.-T. et al. (2012) "Reactive Polymer Coatings: a General Route t Thiol-ene and Thiol-yne Click Reactions" Macromol. *Rapid Commun.* 33:922-927.
Yan, J. et al. (Oct. 8, 2013). "Growing Hyperbranched Polymers Using Natural Sunlight", *Scientific Reports* 3(2841):1-7.
Lee, S. et al. (2016; e-published on Nov. 23, 2015). "Fabrication of PEG-Carboxymethylcellulose Hydrogel by Thiol-norbornene Photoclick Chemistry," *International Journal of Biological Macromolecules* 83:1-8.
Xiang, Z. et al. (Sep. 2013; e-published on Aug. 4, 2013). "Adding an Unnatural Covalent Bond to Proteins Through Proximity-enhanced Bioreactivity," *Nature Methods* 10(9):885-888 (also includes the Erratum—Corrected after Print on Nov. 21, 2013).
U.S. Non Final Office Action dated Nov. 1, 2017, for U.S. Appl. No. 15/409,392, filed Jan. 18, 2017, 19 pages.
U.S. Notice of Allowance dated Apr. 23, 2018, for U.S. Appl. No. 15/409,392, filed Jan. 18, 2017, 10 pages.

DEGRADABLE THIOL-ENE POLYMERS

CROSS-REFERENCE TO RELATED APPLICATIONS

This application is a continuation of U.S. patent application Ser. No. 14/848,141, filed Sep. 8, 2015, which is a continuation of U.S. patent application Ser. No. 14/485,490, filed Sep. 12, 2014, which is a continuation of U.S. patent application Ser. No. 13/951,268, filed Jul. 25, 2013, now U.S. Pat. No. 8,859,716, which is a continuation application of U.S. patent application Ser. No. 12/556,640, filed Sep. 10, 2009, now U.S. Pat. No. 8,519,086, which is a divisional of U.S. patent application Ser. No. 11/858,062, filed Sep. 19, 2007, which is a divisional of U.S. patent application Ser. No. 10/269,916, filed Oct. 10, 2002, now U.S. Pat. No. 7,288,608, which claims priority under 35 U.S.C. § 1.19(e) from U.S. Provisional Application Ser. No. 60/328,669, filed Oct. 10, 2001, all of which are incorporated herein by reference in their entirety.

STATEMENT REGARDING FEDERALLY FUNDED RESEARCH

The U.S. Government has a paid-up license in this invention and the right in limited circumstances to require the patent owner to license others on reasonable terms as provided for by the terms of Grant No. CTS 945-3369 awarded by the National Science Foundation.

FIELD OF THE INVENTION

The invention is directed to the production of degradable thiol-ene based polymers via photopolymerization.

BACKGROUND OF THE INVENTION

Recent approaches in the field of tissue engineering involve the use of polymeric biomaterials as cell scaffolds, which provide cells with a three-dimensional support material on which to grow. Despite a recent expansion in the design and development of suitable scaffold materials, there is still a lack of suitable scaffold materials with systematically variable properties. Without suitable materials available with a wide range of properties to serve as scaffolds for tissue engineering, it is unlikely that the field will achieve its full potential.

Advances in polymer chemistry and materials science have spawned the development of numerous biomaterials and scaffolding methods that have potential uses in a wide range of tissue engineering applications. Several criteria must be achieved in the design of a biomaterial. First, the material must be biocompatible. That is, it must not promote an immune, allergenic, or inflammatory response in the body. Also, a method must exist to reproducibly process the material into a three-dimensional structure. Adhesive properties of the surface of the biomaterial must permit cell adhesion and promote growth. In addition, the biomaterial should have a high porosity to facilitate cell-polymer interactions, improve transport properties, and provide sufficient space for extracellular matrix generation. Finally, depending upon the particular application, the biomaterial should be biodegradable with an adjustable degradation rate so that the rate of tissue regeneration and the rate of scaffold degradation can be matched.

Natural materials, such as collagen and many polysaccharides, generally exhibit a limited range of physical properties, are difficult to isolate, and cannot be manufactured with a high degree of reproducibility. However, natural materials often are more biocompatible and may even have specific biologic activity. Synthetic materials, on the other hand, can be cheaply and reproducibly processed into a variety of structures and the mechanical strength, hydrophilicity, and degradation rates of synthetic scaffolds are more readily tailored. However, synthetic polymers can cause inflammatory responses when implanted in the host. Recent tissue engineering endeavors have attempted to combine properties of both natural and synthetic polymers in the design of a suitable scaffold.

Polylactide (PLA), polyglycolide (PGA) and their copolymers (PLGA) are polyesters based on naturally occurring lactic and glycolic acids ($\alpha$-hydroxy acids). They have been used as biodegradable sutures and implantable materials for more than two decades. They are biocompatible and biodegradable, and these polymers have a history of use as polymer scaffolds in tissue engineering. However, their highly crystalline and hydrophobic nature makes it difficult to control their biodegradation process and mechanical properties. Moreover, because of the lack of pendant functional groups, it is extremely difficult to modify the surface chemistry of PLA and PGA. For example, proteins and other molecules that may facilitate cell adhesion and growth cannot be easily attached to the backbone of these polymers because there is no chemical "handle" with which to derivatize these substrates. Attempts to introduce functional groups into these types of polymers include copolymerization of the lactide and glycolide cyclic monomers with more easily derivatizable monomers such as cyclic lysine monomers modified by peptide attachments.

Recently, alternating copolymers of $\alpha$-hydroxy acids and $\alpha$-amino acids (polydepsipeptides) have been obtained with functional side groups. Additionally, poly(L-lactides) containing $\beta$-alkyl $\alpha$-malate units have been prepared by ring opening copolymerization of L-lactide with a cyclic diester. Major drawbacks remain with these lactide based copolymers including the difficulty in synthesis of cyclic monomers that are used in the copolymerization with lactide and the generally low reaction yields. Thus, the difficult synthesis and the low reaction yields make the commercialization of the modified polylactide biomaterials improbable and make it nearly impossible to tailor chemical, physical, and degradation properties of the final polymer.

Photopolymerization systems have numerous advantages for matrix production. First, photoinitiation allows facile control over the polymerization process with both spatial and temporal control. For example, a liquid macromer solution can be injected into an area of the body, formed into a particular shape, and photopolymerized on demand using a light source. The final polymer hydrogel maintains the shape of that specific area of the body, allowing intimate control over the final shape of the hydrogel and improved adhesion and integration. In addition, the photocrosslinking chemistry creates covalently crosslinked networks that are dimensionally stable.

Known photopolymerization processes, however, suffer from a number of drawbacks, including: the use of a separate initiator specie that is cytotoxic at relatively low concentrations, the difficulty in polymerizing thick samples because of light attenuation by the initiator, the inhibition of the radical polymerization by oxygen present in the air (which slows the polymerization), and the ability to fabricate gels with a diverse range of properties, especially gels with a high water content while maintaining high mechanical strength. Thus, there exists a need for biocompatible hydrogels which can polymerize in the absence of cytotoxic initiators and which can be tailored to have specific chemical, physical, and degradation properties under physiological conditions.

SUMMARY OF THE INVENTION

One embodiment of the present invention is a polymeric material having repeating units of the formula: —[—S—$R_1$—S—C—C—$R_2$—C—C—]—, wherein $R_1$ and $R_2$ are independent linkers, and at least one of $R_1$ and $R_2$ are degradable. $R_1$ and $R_2$ can be independently selected from polylactic acid), poly(ethylene glycol), polyvinyl alcohol), and mixtures thereof, and one or both of $R_1$ and $R_2$ can have a degree of branching of greater than two. The polymeric material is preferably biocompatible, and can have a minimum dimension of at least about 4 cm.

The polymeric materials of the present invention can be produced by a process that includes combining a first reactant of the formula $R_1B(C=C)_n$ with a second reactant of the formula $R_2B(SH)_m$, wherein n and m are independently integers greater than one and $R_1$ and $R_2$ are as described above. The combined reactants are then irradiated with light to cause reaction between the first and second reactants and eventually between the formed products to obtain the polymeric material. This process can include irradiating the reactants in the absence of a chemical initiator.

In a further embodiment, the polymeric material can include at least one biologically active component encapsulated within it. The biologically active component can be selected from the group consisting of cells, tissues, and tissue aggregates, such as chondrocytes, immortalized cell lines, stem cells, hormone-producing cells, or fibroblasts. Additionally, the biologically active component can include pharmacologically active agents or agricultural chemicals. Pharmacologically active agent functional molecules can include analgesics, antipyretics, nonsteriodal antiinflammatory drugs, antiallergics, antibacterial drugs, antianaemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, or coenzymes. Agricultural chemical functional molecules can include fungicides, herbicides, fertilizers, pesticides, carbohydrates, nucleic acids, organic molecules, or inorganic biologically active molecules.

In another embodiment, the polymeric material can be derivatized with a functional molecule, for example, by forming the polymeric material with excess thiol groups and reacting the functional molecule with such excess thiol groups. The functional molecules can be, for example, proteins, agricultural chemicals, or pharmacologically active agents. Protein functional molecules can include adhesion peptides, growth factors, hormones, antihormones, signaling compounds, serum proteins, albumins, macroglobulins, globulins, agglutinins, lectins, antibodies, antigens, enzymes, or extracellular matrix proteins. The polymeric material of the present invention can also be configured to form a degradable commodity plastic.

A further embodiment of the present invention includes a thiol-ene hydrogel having polylactic acid), polyethylene glycol), and polyvinyl alcohol) polymeric segments, wherein at least one of the segments has a degree of branching of greater than two. In this embodiment, the thiol-ene hydrogel has a modification selected from encapsulation of at least one biologically active component within the thiol-ene hydrogel and derivatization of the thiol-ene hydrogel with a functional molecule.

BRIEF DESCRIPTION OF TUE DRAWINGS

DETAILED DESCRIPTION OF THE INVENTION

The present invention is directed to a novel class of degradable scaffolds which are biocompatible thiol-ene hydrogels built upon degradable materials, such as PVA, PEG and PLA blocks, that can incorporate chemicals and live cells within the polymer matrix.

Thiol-ene polymerizations are photochemically initiated, step growth, free-radical processes that take place between thiols and olefins via a sequential propagation/chain-transfer process. For polymerization to occur, each thiol-containing component must have an average of at least two thiol groups and each olefin-containing component must have at least two ene functional groups, (i.e. the monomer must contain two or more double bonds). Polymerization of a dithiol and a diene results in the formation of a linear polymer, rather than a crosslinked polymer. Crosslinked gels can be readily formed by increasing the functionality, i.e., increasing the degree of branching, of one or both of the monomers to be greater than two. Thiol-ene polymerizations have a number of significant and unique advantages that make them particularly beneficial. These benefits include a step growth polymerization that causes the molecular weight to build up more slowly, the ability to photoinitiate the sample without any need for a distinct (and possibly cytotoxic) initiator specie, the ability to polymerize extremely thick (more than 30 cm) samples because of a self-eliminating light intensity gradient, the very low radical concentration present during polymerizations producing less cellular damage from the free radicals, the lack of oxygen inhibition and the ease with which monomers of significantly varying chemistry can be copolymerized.

Thiol-ene systems form ground state charge transfer complexes, and therefore photopolymerize even in the absence of initiators in reasonable polymerization times. Since the complex which absorbs the light is consumed by the polymerization, the polymer itself does not absorb light. Thus, polymerization can proceed to extremely great depths, and no potentially toxic initiator is required to initiate the polymerization. The polymer properties can be tailored by appropriate monomer choices since the products are regular, alternating copolymers. Nearly any unsaturated monomer can polymerize via this mechanism in the presence of a suitable polythiol and light.

Figure 1:
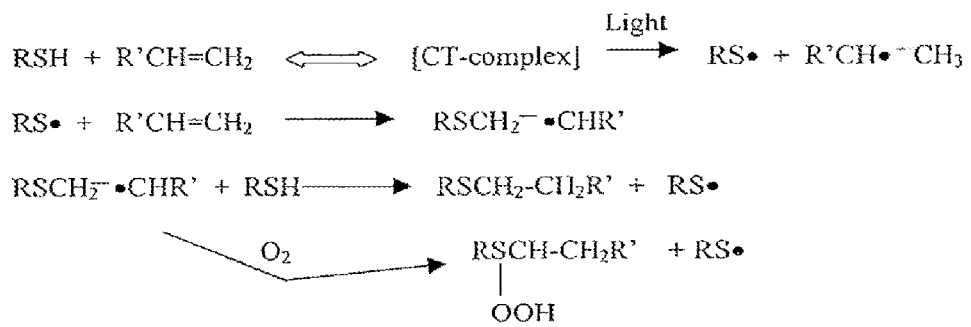
FIG. 1 shows the general scheme for thiol-ene polymerization.

The scheme shown in FIG. 1 is the general polymerization mechanism. The charge transfer complex forms by the interaction of the thiol group with the double bond of the ene followed by electron transfer and formation of a thiyl radical upon exposure to light. The thiyl radical then initiates the polymerization. Termination involves radical-radical combinations of either β-carbon radicals or thiyl radicals.

One embodiment of the present invention is a polymeric material comprising repeating units of the formula:

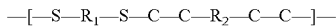

wherein $R_1$ and $R_2$ are independent linkers, and at least one of $R_1$ and $R_2$ are degradable. Thus, the chemical natures of $R_1$ and $R_2$ are independent, that is, they can be the same or different. $R_1$ and $R_2$ function as linkers to link together the thiol-ene junctures. In accordance with the present invention, the polymeric material is preferably produced by a process of combining a first reactant of the formula $R_1$—$(C{=}C)_n$ with a second reactant of the formula $R_2$—$(SH)_m$, wherein n and m are independently integers greater than one and $R_1$ and $R_2$ are as defined above. The first and second reactants are then irradiated with light to cause reaction between the first and second reactants to form the polymeric material. In alternative embodiments, the polymeric material of the present invention can include additional linker segments, $R_3 \ldots R_n$. Such additional linker segments meet the requirements set forth herein for $R_1$ and $R_2$. For example, a polymeric material having the repeating unit described above can further comprise repeating units of the formula:

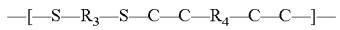

wherein $R_3$ and $R_4$ are independent linkers.

As used herein, the term "degradable," with reference to the $R_1$ and $R_2$ segments and the polymeric materials of the present invention refers to a segment or material having a molecular structure which can decompose to smaller molecules. Such degradation or decomposition can be by various chemical mechanisms. For example, a degradable polymer can be hydrolytically degradable in which water reacts with the polymer to form two or more molecules from the polymer by chemical bonds in the molecule being hydrolyzed, thus producing smaller molecules. In a further embodiment of the present invention, the segments or materials are biodegradable. Biodegradability refers to a compound which is subject to enzymatic decomposition, such as by microorganisms, or to a compound, portions of which are subject to enzymatic decomposition, such as by microorganisms.

$R_1$ and $R_2$, while at least one is degradable, can be chemically diverse. In preferred embodiments, $R_1$ and $R_2$ can be selected from poly(lactic acid) (PLA), polyglycolide (PGA), copolymers of PLA and PGA (PLGA), poly(vinyl alcohol) (PVA), poly(ethylene glycol) (PEG), poly(ethylene oxide), poly(ethylene oxide)-co-poly(propylene oxide) block copolymers (poloxamers, meroxapols), poloxamines, polyanhydrides, polyorthoesters, poly(hydroxy acids), polydioxanones, polycarbonates, polyaminocarbonates, poly(vinyl pyrrolidone), poly(ethyl oxazoline), carboxymethyl cellulose, hydroxyalkylated celluloses such as hydroxyethyl cellulose and methylhydroxypropyl cellulose, and natural polymers such as polypeptides, polysaccharides or carbohydrates such as polysucrose, hyaluronic acid, dextran and similar derivatives thereof, heparan sulfate, chondroitin sulfate, heparin, or alginate, and proteins such as gelatin, collagen, albumin, or ovalbumin, or copolymers, or blends thereof. In particularly preferred embodiments, $R_1$ and $R_2$ can be selected from polylactic acid) (PLA), poly(vinyl alcohol) (PVA), and poly(ethylene glycol) (PEG). PLA monomers provide degradability to the system while PVA and PEG enhance the hydrophilic nature of the hydro gel and provide for the possibility of further derivatization and/or extensive crosslinking.

$R_1$ and $R_2$ can vary in size depending upon desired properties for the resulting polymeric material. More particularly, the molecular weight for $R_1$ and $R_2$ can range from about 30 DA to about 50000 Da. Prior to formation of the polymeric material of the present invention, $R_1$ and $R_2$ are derivatized to include thiol or olefin moieties such that they can participate in photo-initiated thiol-ene polymerization. Thiolated macromers such as polyethylene glycol) dithiol are available commercially. The olefin moieties can be selected from any suitable compound having a carbon double bond. For example, the olefin moiety can be selected from any suitable ethylenically unsaturated group such as vinyl, acetyl, vinyl ether, allyl, acrylate, methacrylate, maleimide, and norbornene. Thus, it will be appreciated that in the repeating unit shown above, the carbons can be $CH_2$ or can be substituted at one or more than one of the carbons within the repeating group, even including ring structures incorporating a double bond. If each of $R_1$ and $R_2$ are derivatized with either two thiol or two olefin moieties, the resulting thiol-ene polymer would be a linear copolymer composed of alternating $R_1$ and $R_2$ segments. However, the thiol-ene polymeric material is preferably formed to contain cross-linking and branching. Thus, the derivatized $R_1$ and $R_2$ segments preferably have more than two thiol or olefin moieties per molecule that can participate in crosslinking and polymerization. The extent of the branching and cross-linking can be controlled by the use of differently derivatized $R_1$ and $R_2$ segments and control over the concentration of the starting materials.

By photoinitiation of the thiol-ene polymerization reaction with these monomeric, oligomeric or polymeric starting materials, high molecular weight, crosslinked networks are obtainable in the presence or absence of a chemical initiator within reasonable reaction times. This is a very important property inherent to the polymerization reactions, which can eliminate the adverse effects of chemical initiators and still obtain rapid curing. Because of the step growth nature of the polymerization, these polymers have significantly lower glass transition temperatures and higher degrees of swelling than homopolymer diacrylate analogues. Thus, simple changes in molecular weight, number of functional groups, and the chemistry of the monomer between the functional groups allow facile control of the polymer properties over a wide range.

Figure 2:
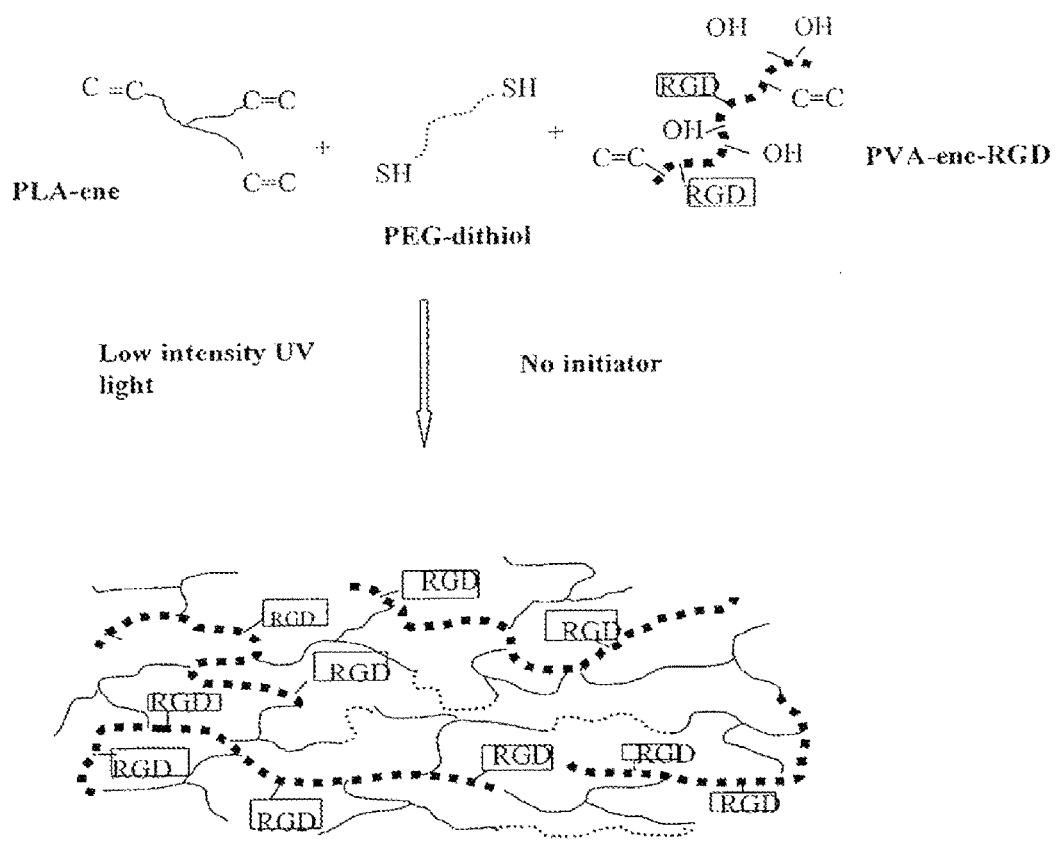
FIG. 2 shows a scheme for the formation of a thiol-ene hydrogel formed from derivatized PLA, PEG and PVA monomers.

FIG. 2 illustrates an example of a thiol-ene hydrogel that can be formed from derivatized PLA, PEG and PVA monomers. The resulting hydrogel is formed from the PLA triene (e.g., made from glycerol with three lactide arms and subsequent ene attachment), the PEG dithiol (such as the commercially available PEG dithiol), and the partially acrylated PVA derivatized to include the well-known RGD adhesion sequence. Hydrogel matrices of this type facilitate independent control of the (i) mechanical properties by adjusting the PVA and PLA functionality, (ii) swelling through adjustments to the relative amount of PEG, (iii) the degradation timescale through adjustments in the molecular weight of the PLA arms, and (iv) attachment of biomolecules such as signaling compounds to the PVA backbone. The resulting networks will be three dimensional, hydrophilic, porous structures that can be further modified by the attachment of molecules of interest to the pendant —OH groups of PVA to impart therapeutic or other properties to the hydrogel. Thiol-ene polymers are alternating copolymers, but because a monomer can be derivatized in numerous ways, the ability to vary the composition of the copolymers exists.

A list of some properties of the thiol-ene hydrogel illustrated in FIG. 2 that can be influenced by modifying parameters of the individual monomers is shown in Table 1.

Degradation rate, mechanical properties, crosslink density and swelling can each be controlled with systematic changes in the amounts, molecular weights or functionality of the various monomers. For example, in considering control of the degradation rate of the polymer matrix, the simplest method for controlling this feature is to change the molecular weight of the oligomeric PLA branches. The higher the molecular weight of the branch, the more rapidly the system will degrade. This phenomena, which is different from what might be observed in linear PLA systems, arises because the PLA segments may act as crosslinks in the system. As the molecular weight of the PLA crosslink increases, the probability that any one of the repeat units and hence the crosslink will be degraded is higher, thus leading to more rapid degradation of the PLA crosslinks.

TABLE 1

Influence of Monomer Amounts and Structural Features on the Polymer Matrix Properties

| Monomer Parameters to be Varied | Primary Influence | Secondary Influence |
| --- | --- | --- |
| Molecular Weight of PLA Branches | Degradation Rate | Swelling (minor) |
| Number of PLA Branches per PLA Monomer (i.e., the functionality) | Crosslink Density Mechanical Properties | Swelling |
| Amount of PLA Monomer | Crosslink Density Mechanical Properties | Swelling (minor) |
| Degree of Substitution on PVA Backbone | Crosslink Density Mechanical Properties | Swelling - also changes because of consumption of hydrophilic —OH functional groups |
| Amount of PEG Monomer | Swelling | Crosslink Density (minor) |

Another parameter that dictates the network properties is monomer functionality. For example, in the example shown in FIG. 2, as the number of reactive functional groups on the PLA branched oligomer or PVA increases, the extent of crosslinking increases, giving more rigid hydrogels. Increasing the functionality of the PVA monomers requires consuming additional —OH functional groups and converting them to thiols or vinyl substituents. The loss of hydroxyl functional groups reduces the network hydrophilicity to a minor degree, thus impacting the swelling. Additionally, for both of these changes, the increase in crosslink density impacts the initial equilibrium swelling; however, the swelling is more easily controlled by the amount of PEG added to the matrix. The functionality of the PLA will be adjusted by starting with di-, tri-, and tetra-functional alcohols in the PLA synthesis to obtain di-, tri- and tetra-functional oligomers oligomers with two, three and four branches). The size of the oligomer chains is controlled during the synthesis by changing the ratio of hydroxyl groups to lactides. The PVA functionality can be manipulated by replacing between about 2% and about 10% of the hydroxyl functional groups with vinyl or thiol groups.

As noted above, the thiol-ene hydrogels of the present invention are prepared from biocompatible monomers. A biocompatible material does not promote an immune, allergenic or inflammatory response in the body. The resulting hydrogels are therefore biocompatible as well and can be used internally for the purposes of tissue engineering. Because the individual monomers are biocompatible and the polymerization process itself can be free of toxic chemical initiators, it is also possible to encapsulate biologically active materials, such as cells, tissue and tissue aggregates during the polymerization process thereby trapping such materials within the biocompatible hydrogel matrix. These materials are then supported within the matrix and can function within the correct temperature, water and nutrient environment. Cells of interest for encapsulation include chondrocytes, immortalized cell lines, stem cells, hormone-producing cells, fibroblasts and the like. To have an optimal cell environment, the hydrophilicity and transport properties (e.g. diffusion) must be controlled. In particular, the matrices must allow for the ready transport of nutrients and oxygen to encapsulated cells, as well as the removal of cellular waste products. Suitable matrices include multi-branched PLA and PVA chains either linked to each other or to PEG segments to form a three dimensional structure. PEG is extremely hydrophilic. Therefore, the presence of large amounts of PEG (as well as the remaining hydroxyls from the PVA) assure that the degree of swelling of the hydrogel is high and that transport is facile.

In a further embodiment of the present invention, monomers are synthesized that contain chemical links to allow for derivatization of the polymeric material with functional molecules as well as the necessary thiol and olefin moieties for formation of the hydrogel. For example, the monomers could be derivatized to contain multiple thiol groups, some of which are derivatized to link a protein while others are left free to participate in the thiol-ene polymerization thereby forming a thiol-ene hydrogel containing bound protein. Alternatively, a thiol-ene hydrogel can be produced with monomers having an excess of thiol groups and after formation, the hydrogel can be derivatized with a protein.

Knowledge of the biological events that occur at the cell-scaffold interface plays a key role in tissue engineering. Vital interactions occur on the molecular scale, and the proteins and factors that are responsible for these interactions may be incorporated into suitable scaffolding materials by derivatization of the polymeric material of the present invention. For example, signaling molecules, hormones, and growth factors each can be integrated into the hydrogel through derivatization of the monomers, macromers or polymers, thereby mimicking the native environment (i.e., in the body) of those cells, resulting in more efficient production of extracellular matrix and improved tissue-like properties of the final material. One of the significant advantages of the thiol-ene approach is the simplicity with which the resulting polymeric networks can be derivatized. The thiols can be easily modified either before or after polymerization (if a slight excess of thiol is added to the polymerization, a significant number of thiols will remain unreacted and derivatizable).

A wide variety of molecules can be incorporated into the polymeric material through —OH groups or —SH groups including, but not limited to, proteins, pharmacologically active agents, and agricultural chemicals. Alternatively, such molecules can be encapsulated in the polymeric material in the event such molecules would lose functionality if chemically bound to the polymeric material. For example, types of proteins that can be incorporated into the polymeric material include adhesion peptides (such as RGD adhesion sequence), growth factors, hormones, antihormones, signaling compounds, enzymes, serum proteins, albumins, macroglobulins, globulins, agglutinins, lectins, extracellular matrix proteins, antibodies, and antigens. Types of pharmacologically active agents that can be incorporated into the polymeric material include analgesics, antipyretics, nonsteriodal antiinflammatory drugs, antiallergics, antibacterial drugs, antianemia drugs, cytotoxic drugs, antihypertensive drugs, dermatological drugs, psychotherapeutic drugs, vitamins, minerals, anorexiants, dietetics, antiadiposity drugs, carbohydrate metabolism drugs, protein metabolism drugs, thyroid drugs, antithyroid drugs, and coenzymes. Types of agricultural chemicals that can be incorporated into the polymeric material include fungicides, herbicides, fertilizers, pesticides, carbohydrates, nucleic acids, organic molecules, and inorganic biologically active molecules. In a further embodiment, the polymeric material of the present invention can be formed as commodity plastic products that are typically considered to be disposable products. Because the polymeric material of the present invention is degradable, such products, when disposed of, will more rapidly degrade in the environment. Such products include, for example, eating utensils, plates, bowls, cups, food and beverage containers and packaging.

The following experimental results are provided for purposes of illustration and are not intended to limit the scope of the invention.

EXAMPLES

Example 1

This example shows two possible derivatizations of poly(vinyl alcohol).

Figure 3:
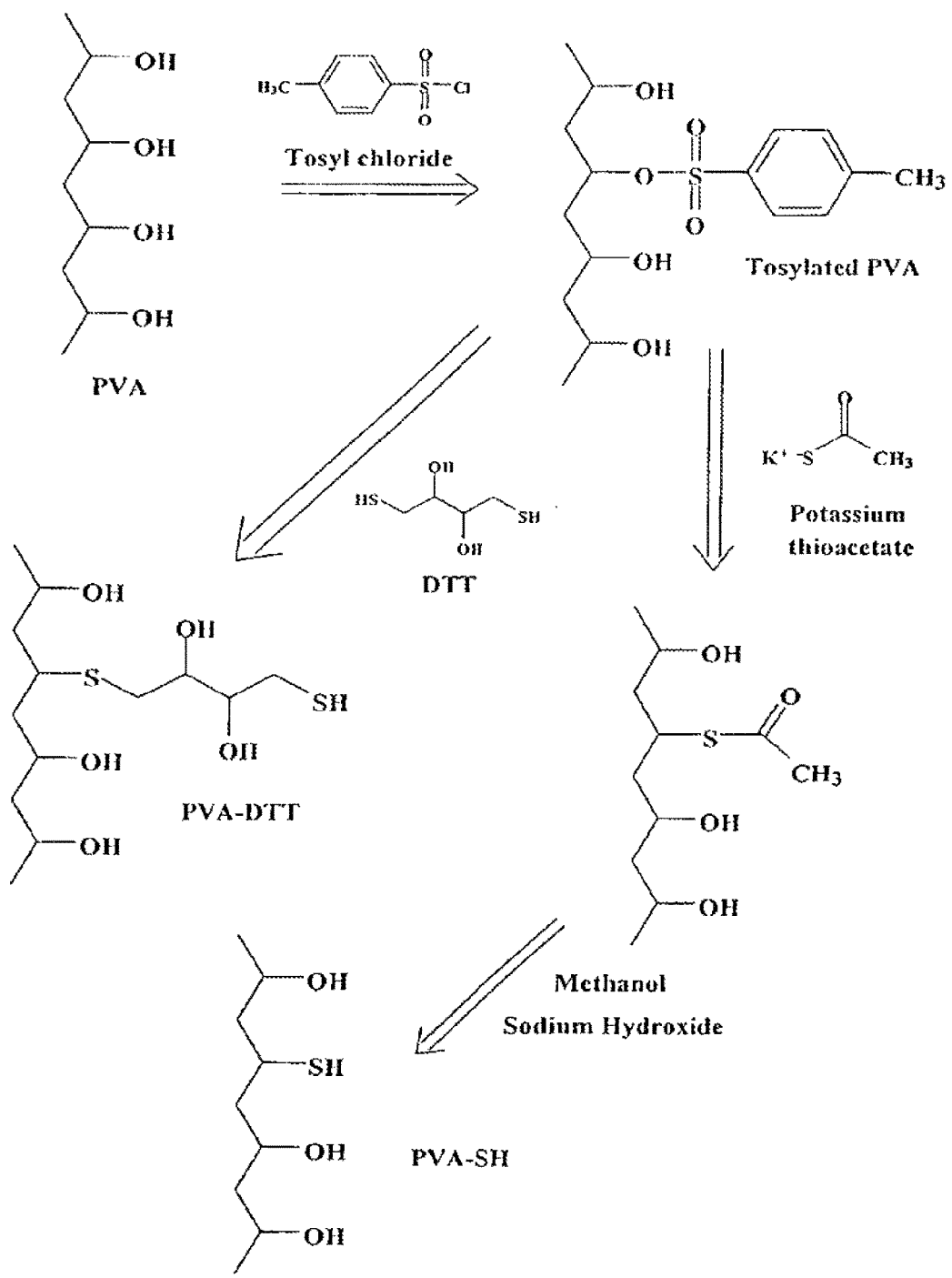
FIG. 3 shows schemes for derivatizations of poly(vinyl alcohol).

Synthesis of a thiol macromer can proceed via several approaches, two of which are presented in the scheme shown in FIG. 3. Both progress via a tosylate intermediate. Poly (vinyl alcohol) was tosylated in anhydrous pyridine at 85° C. overnight. The insoluble PVA was pulled into solution as the reaction proceeded. This tosylated PVA was then be reacted with dithiothreitol (DTT), in one instance, and potassium thioacetate, in another instance, at room temperature. Nucleophilic attack of the thiolate anion displaced the tosyl group, covalently linking these molecules to the PVA backbone through a thioether bond. PVA-thioacetate was hydrolyzed via simple methanolysis, yielding the thiol macromer (PVA-SH) in which the thiol groups have replaced some of the hydroxyl groups. Using an excess of DTT in the other mechanism guarantees that there will be free thiol groups in the resulting molecule (PVA-DTT).

Once formed, the thiolated PVA can then be photopolymerized in the presence of a multi-ene in an aqueous solution to provide a crosslinked hydrogel network. Polymerizations of the thiolated. PVA with the PLA triacrylate or PLA triallyl yield a degradable, hydrogel network in which the swelling and degradation time are controlled by the amount and molecular weight of the trifunctional PLA, respectively.

Example 2

This example demonstrates the feasibility of synthesizing PLA multi-ene and PLA multithiol monomers for use in the present invention.

Figure 4:
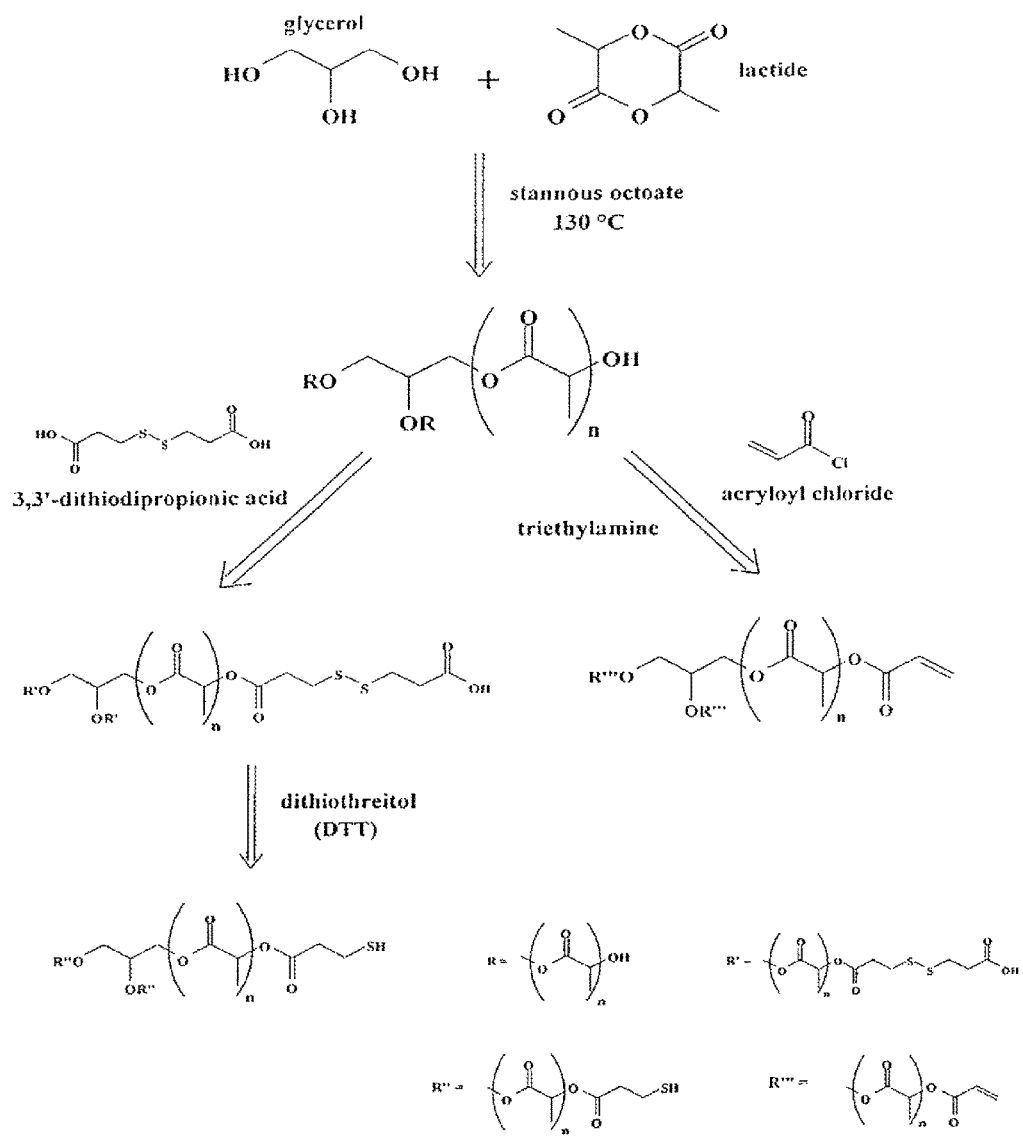
FIG. 4 shows schemes for derivatizations of poly(lactic acid).

A major advantage of thiol-ene hydrogels is the ability to use a wide range of precursor molecules with varying structures and chemistries. In particular, the technique affords the possibility of having largely polylactic acid) polymers in which the degradation rate is controlled by the PLA segment molecular weight. To obtain this control, it is necessary to synthesize PLA multi-enes and PLA multithiols. FIG. 4 shows the scheme for the synthesis of PLA trithiol and PLA triacrylate.

Lactic acid oligomers with three branches were prepared with glycerol used as an initiator to polymerize the lactide using stannous octoate as the catalyst. Oligomers with different chain lengths were obtained by adjusting the initiator/lactide ratio. This oligomer was used to derivatize the hydroxyl end groups of the three branches either with acrylates or with thiols. None of the PLA thiol derivatives have previously been synthesized. Synthesized macromers were characterized by FTIR and NMR. PLA triacrylate showed all the reported IR and $^1$H-NMR bands.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the claims below.

What is claimed is:

1. A method for producing a hydrogel comprising a biocompatible cross-linked degradable thiol-ene polymer, the method comprising:
   subjecting a polymerization reaction mixture comprising at least one thiol compound and at least one olefin compound to a radical polymerization reaction under conditions sufficient to produce the biocompatible cross-linked degradable thiol-ene polymer, wherein
   (a) the at least one thiol compound comprises m number of reactive thiol groups;
   (b) the at least one olefin compound comprises n number of reactive ene groups, wherein at least one of the ene groups is a norbornene moiety; and
   (c) each of n and m is an integer of at least 2, provided that the sum of n+m is at least 5.

2. The method of claim 1, wherein the at least one olefin compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a carboxymethyl cellulose; a hydroxyalkylated cellulose; a polypeptide; a polysaccharide; a carbohydrate; heparan sulfate; chondroitin sulfate; heparin, alginate; and a combination thereof.

3. The method of claim 1, wherein the at least one thiol compound comprises a polymeric moiety selected from the group consisting of poly(lactic acid) (PLA); polyglycolide (PGA); a copolymer of PLA and PGA (PLGA); poly(vinyl alcohol) (PVA); poly(ethylene glycol) (PEG); poly(ethylene oxide); a poly(ethylene oxide)-co-poly(propylene oxide) block copolymer; a poloxamine; a polyanhydride; a polyorthoester; a poly(hydroxy acids); a polydioxanone; a polycarbonate; a polyaminocarbonate; a poly(vinyl pyrrolidone); a poly(ethyl oxazoline); a carboxymethyl cellulose; a hydroxyalkylated cellulose; a polypeptide; a polysaccharide; a carbohydrate; heparan sulfate; chondroitin sulfate; heparin, alginate; and a combination thereof.

4. The method of claim 1, wherein the at least one thiol compound is a branched thiol compound.

5. The method of claim 1, wherein the at least at least one olefin compound is a branched olefin compound.

6. The method of claim 1, wherein the polymerization reaction mixture further comprises a chemical initiator.

7. The method of claim 1, wherein the polymerization reaction mixture further comprises a biologically active component.

8. The method of claim 7, wherein the biologically active component is selected from the group consisting of cells, tissues, and tissue aggregates.

9. The method of claim 7, wherein the biologically active component is selected from the group consisting of chondrocytes, immortalized cell lines, stem cells, hormone-producing cells and fibroblasts.

10. The method of claim 7, wherein the biologically active component is selected from the group consisting of a protein, a pharmacologically active agent, and an agricultural chemical.

11. The method of claim 10, wherein the biologically active component is a protein selected from the group consisting of an adhesion peptide, growth factor, hormone, antihormone, signaling compound, enzyme, serum protein, albumin, macroglobulin, globulin, agglutinin, lectin, extracellular matrix protein, antibody, antigen, and a combination thereof.

12. The method of claim 10, wherein the biologically active component is a pharmacologically active agent selected from the group consisting of an analgesic, antipyretic, nonsteriodal antiinflammatory drug, antiallergic, antibacterial drug, antianemia drug, cytotoxic drug, antihypertensive drug, dermatological drug, psychotherapeutic drug, vitamin, mineral, anorexiant, dietetic, antiadiposity drug, carbohydrate metabolism drug, protein metabolism drug, thyroid drug, antithyroid drug, coenzymes, and a combination thereof.

13. The method of claim 10, wherein the biologically active component is an agricultural chemical selected from the group consisting of a fungicide, herbicide, fertilizer, pesticide, carbohydrate, nucleic acid, organic molecule, inorganic biologically active molecule, and a combination thereof.

14. The method of claim 7, wherein the radical polymerization reaction encapsulates the biologically active component within the biocompatible cross-linked degradable thiol-ene polymer.

15. The method of claim 2, wherein the polymeric moiety has a molecular weight ranging from about 30 Da to about 50,000 Da.

16. The method of claim 3, wherein the polymeric moiety has a molecular weight ranging from about 30 Da to about 50,000 Da.

17. The method of claim 2, wherein the polymeric moiety is biodegradable.

18. The method of claim 3, wherein the polymeric moiety is biodegradable.

19. The method of claim 2, wherein the polymeric moiety selected from the group consisting of poly(lactic acid) (PLA), poly(vinyl alcohol) (PVA), and poly(ethylene glycol) (PEG), and a combination thereof.

20. The method of claim 3, wherein the polymeric moiety selected from the group consisting of poly(lactic acid) (PLA), poly(vinyl alcohol) (PVA), and poly(ethylene glycol) (PEG), and a combination thereof.

21. A method for producing a biocompatible thiol-ene hydrogel, the method comprising subjecting a polymerization reaction mixture comprising at least one thiol compound and at least one olefin compound to a radical polymerization reaction under conditions sufficient to produce the biocompatible thiol-ene hydrogel, wherein:
(a) the at least one thiol compound comprises m number of reactive thiol groups;
(b) the at least one olefin compound comprises n number of reactive ene groups; and
(c) each of n and m is an integer of at least 2, provided the sum of n+m is at least 5.

22. The method of claim 21 wherein the at least one thiol compound comprises a polymeric moiety selected from the group consisting of poly(lactic acid) (PLA), polyglycolide (PGA), a copolymer of PLA and PGA (PLGA), poly(vinyl alcohol) (PVA), poly(ethylene glycol) (PEG), poly(ethylene oxide), a poly(ethylene oxide)-co-poly(propylene oxide) block copolymer, a poloxamine, a polyanhydride, a polyorthoester, a poly(hydroxy acids), a polydioxanone, a polycarbonate, a polyaminocarbonate, a poly(vinyl pyrrolidone), a poly(ethyl oxazoline), a carboxymethyl cellulose, a hydroxyalkylated cellulose, a polypeptide, a polysaccharide, a carbohydrate, heparan sulfate, chondroitin sulfate, heparin, alginate, hyaluronic acid, gelatin, and a combination thereof.

23. The method of claim 22, wherein the at least one thiol compound comprises a polymeric moiety selected from the group consisting of hyaluronic acid and gelatin.

24. The method of claim 23, wherein the polymeric moiety of the at least one thiol compound is hyaluronic acid.

25. The method of claim 23, wherein the polymeric moiety of the at least one thiol compound is gelatin.

26. The method of claim 21, wherein the at least one olefin compound comprises a polymeric moiety selected from the group consisting of poly(lactic acid) (PLA), polyglycolide (PGA), a copolymer of PLA and PGA (PLGA), poly(vinyl alcohol) (PVA), poly(ethylene glycol) (PEG), poly(ethylene oxide), a poly(ethylene oxide)-co-poly (propylene oxide) block copolymer, a poloxamine, a polyanhydride, a polyorthoester, a poly(hydroxy acids), a polydioxanone, a polycarbonate, a polyaminocarbonate, a poly (vinyl pyrrolidone), a poly(ethyl oxazoline), a carboxymethyl cellulose, a hydroxyalkylated cellulose, a polypeptide, a polysaccharide, a carbohydrate, heparan sulfate, chondroitin sulfate, heparin, alginate, and a combination thereof.

27. The method of claim 26, wherein the at least one olefin compound comprises a polymeric moiety selected from the group consisting of polypeptide, poly(lactic acid) (PLA), poly(vinyl alcohol) (PVA), and poly(ethylene glycol) (PEG), and a combination thereof.

28. The method of claim 27, wherein the polymeric moiety of the at least one olefin compound is poly(ethylene glycol) (PEG).

29. The method of claim 21, wherein the at least one olefin compound comprises an ene group selected from the group consisting of a vinyl moiety, a vinyl ether moiety, an allyl moiety, an acrylate moiety, a methacrylate moiety, a maleimide moiety, and a norbornene moiety.

30. The method of claim 21, wherein the at least one thiol compound is a branched thiol compound.

31. The method of claim 21, wherein the at least at least one olefin compound is a branched olefin compound.

32. The method of claim 21, wherein the ene group is a norbornene moiety.

33. The method of claim 21, wherein the molecular weight of the at least one thiol compound is from about 30 Da to about 50 kDa.

34. The method of claim 21, wherein the molecular weight of the at least one olefin compound is from about 30 Da to about 50 kDa.

35. The method of claim 21, wherein the at least one thiol compound is biodegradable.

36. The method of claim 21, wherein the at least one olefin compound is biodegradable.

37. The method of claim 21, wherein the polymerization reaction mixture further comprises a chemical initiator.

38. The method of claim 21, wherein the polymerization reaction mixture further comprises a biologically active component.

39. The method of claim 38, wherein the biologically active component is selected from the group consisting of cells, tissues, and tissue aggregates.

40. The method of claim 39, wherein the biologically active component is selected from the group consisting of chondrocytes, immortalized cell lines, stem cells, hormone-producing cells and fibroblasts.

41. The method of claim 39, wherein the biologically active component is selected from the group consisting of a protein, a pharmacologically active agent, and an agricultural chemical.

42. The method of claim 41, wherein the biologically active component is a protein selected from the group consisting of an adhesion peptide, growth factor, hormone, antihormone, signaling compound, enzyme, serum protein, albumin, macroglobulin, globulin, agglutinin, lectin, extracellular matrix protein, antibody, antigen, and a combination thereof.

43. The method of claim 41, wherein the biologically active component is a pharmacologically active agent selected from the group consisting of an analgesic, antipyretic, nonsteriodal antiinflammatory drug, antiallergic, antibacterial drug, antianemia drug, cytotoxic drug, antihypertensive drug, dermatological drug, psychotherapeutic drug, vitamin, mineral, anorexiant, dietetic, antiadiposity drug, carbohydrate metabolism drug, protein metabolism drug, thyroid drug, antithyroid drug, coenzymes, and a combination thereof.

44. The method of claim 41, wherein the biologically active component is an agricultural chemical selected from the group consisting of a fungicide, herbicide, fertilizer, pesticide, carbohydrate, nucleic acid, organic molecule, inorganic biologically active molecule, and a combination thereof.

45. The method of claim 38, wherein the radical polymerization reaction encapsulates the biologically active component within the biocompatible thiol-ene hydrogel.

* * * * *